(12) United States Patent
Hewlett et al.

(10) Patent No.: US 8,652,490 B2
(45) Date of Patent: Feb. 18, 2014

(54) PASTEURIA STRAIN

(75) Inventors: Thomas E. Hewlett, High Springs, FL (US); John P. Waters, Lake City, FL (US)

(73) Assignee: Pasteuria Bioscience, Inc., Alachua, FL (US)

( * ) Notice: Subject to any disclaimer, the term of this patent is extended or adjusted under 35 U.S.C. 154(b) by 747 days.

(21) Appl. No.: 12/693,666

(22) Filed: Jan. 26, 2010

(65) Prior Publication Data

US 2010/0189693 A1 Jul. 29, 2010

Related U.S. Application Data

(60) Provisional application No. 61/147,174, filed on Jan. 26, 2009.

(51) Int. Cl.
  *A01N 25/00* (2006.01)
  *A01N 63/00* (2006.01)
  *C12N 1/00* (2006.01)
  *C12N 1/12* (2006.01)
  *C12N 1/20* (2006.01)
  *C12P 1/04* (2006.01)

(52) U.S. Cl.
  USPC ....... 424/252.1; 424/93.4; 424/405; 435/170; 435/243; 435/822

(58) Field of Classification Search
  None
  See application file for complete search history.

(56) References Cited

U.S. PATENT DOCUMENTS

| | | | |
|---|---|---|---|
| 5,089,263 | A | 2/1992 | Spiegel et al. |
| 5,094,954 | A | 3/1992 | Previc et al. |
| 5,248,500 | A | 9/1993 | Ayanaba |
| 5,593,668 | A | 1/1997 | Nishimuta et al. |
| 6,110,904 | A | 8/2000 | Warrior et al. |
| 6,919,197 | B2 | 7/2005 | Gerber et al. |
| 7,067,299 | B2 | 6/2006 | Gerber et al. |
| 2004/0137600 | A1 | 7/2004 | Gerber et al. |

FOREIGN PATENT DOCUMENTS

| | | |
|---|---|---|
| JP | 2000-095627 | 4/2000 |
| WO | WO 99/08534 | 2/1999 |

OTHER PUBLICATIONS

Bajaj, H.K., et al. "Studies on a *Pasteuria* isolate from an entomopathogenic nematode, *Steinernema pakistanense* (Nematoda: Steinernematidae)," *Nematology*, Jun. 2005, pp. 637-640, vol. 7, No. 4.

Bishop, A.H., et al., "Morphological and molecular characteristics of a new species of *Pasteuria* parasitic on *Meloidogyne ardenensis*," *Journal of Invertebrate Pathology*, Feb. 2007, pp. 28-33, vol. 96.

Duan, Y.P., et al. "Detection and characterization of *Pasteuria* 16S rRNA gene sequences from nematodes and soils," *International Journal of Systematic and Evolutionary Microbiology*, 2003, pp. 105-112, vol. 53.

Talavera, M., et al., "Effect of spore inoculum and agricultural practices on the vertical distribution of the biocontrol plant-growth-promoting bacterium *Pasteuria penetrans* and growth of *Meloidogyne incognita*-infected tomato," *Biol Fertil Soils*, 2002, pp. 435-440, vol. 35.

Verdejo, S., et al., "Culture of *Pasteuria* penetrans in Meloidogyne indocnita on oligoxenic excised tomato root culture," *Journal of Nematology*, Oct. 1986, pp. 635, vol. 18, No. 4, Abstract Only.

Ciancio et al. "Observations on a pasteuria isolate parasitic on *Hoplolaimus galeatus* in Peru" *J. Nematology*, 1998, pp. 206-210, vol. 30, No. 2.

Giblin-Davis et al. "Isolates of the Pasteuria penetrans group from phytoparasitic nematodes in bermudagrass turf" *J. Nematol.*, 1990, pp. 750-762, vol. 22, No. 4S.

Giblin-Davis et al. "Ultrastructure and development of two pasteuria species on *Hoplolaimus galeatus*" *J. Nematol.*, 2003, pp. 340, vol. 35, No. 3, Abstract.

Preston et al. "Pasteuria spp.: Systematics and phylogeny of these bacterial parasites of phytopathogenic nematodes" *J. Nematology*, 2003, pp. 198-207, vol. 35, No. 2.

Sharma et al. "Characterization of Pasteuria isolated from *Heterodera cajani* using morphology, pathology and serology of endospores" *Systematic and Applied Microbiology*, 1996, pp. 106-112, vol. 19, No. 1.

Schmidt et al. "Molecular and Morphological Characterization and Biological Control Capabilities of a Pasteuria ssp Parasitizing *Rotylenchulus reniformis*, the Reniform Nematode" *J. Nematology*, 2010, pp. 207-217, vol. 42, No. 3.

*Primary Examiner* — Debbie K Ware
(74) *Attorney, Agent, or Firm* — Saliwanchik, Lloyd & Eisenschenk

(57) ABSTRACT

The subject invention provides a novel and advantageous strain of *Pasteuria* bacteria with nematicidal activity against Reniform nematodes. The subject invention provides the novel bacteria culture referred to as ATCC PTA-9643, and mutants thereof. Also provided are nematicidal compositions comprising the *Pasteuria* strain or its mutants or variants and methods for treating phytopathogenic and soil-dwelling nematodes.

5 Claims, No Drawings

SEQUENCE LISTING

<160> NUMBER OF SEQ ID NOS: 4

<210> SEQ ID NO 1
<211> LENGTH: 1170
<212> TYPE: DNA
<213> ORGANISM: Pasteuria

<400> SEQUENCE: 1
tgcaagtcga gcgcgcactc cttttggggt gcgagcggcg gacgggtgag taacacgtgg 60
ataacctgca cagaagacgg ggattacccc cggaaacggg ggtcaatacc ggatacgcct 120
cctagatcgc atgatccggg agggaaaggt gccttcgggc gccgcttttg gagggatccg 180
cggcgcatta gctagttggt gaggtaaggg ctcaccaagg cgacgatgcg tagccggctt 240
gggagagcgg acggccacac tgggactgag acacggccca gactcctacg ggaggcagca 300
gtagggaatt ttccgcaatg ggcgaaagcc tgacggagcg acgccgcgtg ggtgaagacg 360
gccttcgggt tgtaaagccc tgttcatcgg gaagaagaaa tgacggtacc ggtgaagaaa 420
gccccggcta actacgtgcc agcagccgcg gtaatacgta gggggcgagc gttgtccggg 480
atgattgggc gtaaagggcg tgtaggcgga tacataggtc gggcgtgaaa ggcgcgggct 540
caacccgtgt gagcgttcga aacggtgtgt cttgagtgca gtagagggaa gcggaatttc 600
tggtgtagcg gtggaatgcg tagatatcag aaggaacacc ggtggcgaag gcggcttcct 660
ggactgttac tgacgctgag gcgcgaaggc gtggggagca aacaggatta gataccctgg 720
tagtccacgc ggtaaacgat gagtgctaga tgtagggatg ctcagcatct ttgtgccgaa 780
ggaaacccat taagcactcc gcctggggag tacggtcgca aggctgaaac tcaaaggaat 840
tgacgggggc ccgcacaagc ggtggagcat gtggtttaat tcgatgcaac gcgaagaacc 900
ttaccaaggc ttgacatccc ggtgaaaggc ctcgaaagag tgccgtgccc ccttcggggg 960
gagcatcggt gacaggtggt gcatggttgt cgtcagctcg tgtcgtgaga tgttgggttc 1020
agtcccgcaa cgagcgcaac ccttatctcc ggttgccagc acgtaagggt gggcactttg 1080
gagagacagc cggcgaaagc cggaggaagg cggggacgac gtcaaatcat catgcccctt 1140
atgttttggg ctacacacgt gctacaatgg 1170

<210> SEQ ID NO 2
<211> LENGTH: 252
<212> TYPE: DNA
<213> ORGANISM: Pasteuria

<400> SEQUENCE: 2
tcgtgtttct gtggagatag aggataccca ggtagctatt acggttacag accggggcgt 60
gggaattgta gatgtggagc aggccaggca atctttgtat acttctaggc cagaatggga 120
gcgcgcgggg atggggtttt ccattatgga acatttcatg gatcaggtga gggttcgttc 180

```
tacgcccggt caaggtaccg tagtacatat gataaaaaag ttgcaggcga gtaggaatgt    240
agccgttgcg at                                                       252

<210> SEQ ID NO 3
<211> LENGTH: 764
<212> TYPE: DNA
<213> ORGANISM: Pasteuria

<400> SEQUENCE: 3
cacgtataca cggtttgagt gaagcaatgt ctggcgagct cgttgagttt tctaagggta     60
atctgggaat ggttgcgaac ctggagatgg agaatgtcgg tgttgtggta ctgggatctt    120
gtgatgagat tcatgagggg gaccctgtac gccgtacagg tcggttgatg gaagtaccgg    180
tgggtgaggc attgctgggt cgggtagtca accccctcgg acagccccca gatggggcag    240
ggcctatttc ctcggaacac ttccgtcctg tggaaatgcc agctgcaggt gttgtggatc    300
gccgatctgt tcatcagccc ctgcagacag ggatcaaggc gatcgatgcg atggtgccca    360
ttggtcgcgg gcaacgcgag ttgatcattg gggatcgtca gacggggaaa acgacggttg    420
cggtggatac gatcctgaat cagaaggata cgggtgtcct ttgtgtctac gtagcgattg    480
gtcagaagca gtctacagtg gcgcaggtgg tggagaaatt acgacaacgg ggtgcgatgg    540
agtataccac ggtggtggta gcgagtgctt ccgatcccct tccccttctg tacttagccc    600
cctatgcggg ttgtgtgatg ggcgagtatt ttatgtatca gggtggccat gtgttgtgtg    660
tatacgatga tctttccaag caggctgcgg cctaccggga gctttccctt ttacttcgtc    720
gtccgccagg acgtgaagcc taccccgggg atgttttta ctta                     764

<210> SEQ ID NO 4
<211> LENGTH: 245
<212> TYPE: DNA
<213> ORGANISM: Pasteuria

<400> SEQUENCE: 4
ggtgtcgaaa atgatggagg cacgtacgga gaggattaag tctactctgg aggaggcaga     60
agcgaagcgg aaggaggccc ttctctatgt agagcagtaa agggaggcct tgaagcaagc    120
ccggcaggag gctcagggga tgcttgccac tgcgcgtttt cagaaggagc aggaggcggc    180
gtcgatccta caggaggcga ggcagagagc cgagcaaacg ttggagtctg ctaagtcgga    240
ggttg                                                               245
```

PASTEURIA STRAIN

CROSS-REFERENCE TO A RELATED APPLICATION

This application claims the benefit of U.S. Provisional Application Ser. No. 61/147,174, filed Jan. 26, 2009, the disclosure of which is hereby incorporated by reference in its entirety, including all figures, tables or drawings.

BACKGROUND OF INVENTION

Plant parasitic nematodes inflict crop losses to world agriculture currently estimated to exceed $100 billion annually. Preventing this damage represents a significant challenge. With the impending loss of the fumigant methyl bromide, there is insufficient time to develop and register new synthetic compounds for nematode control.

Phytopathogenic nematodes are particularly difficult to control because they are covered with a thick, impermeable cuticle, or outer covering, and have very few sensory neurons. Since many pest control compounds operate as neurotoxins, the low number of neurons exposed by phytopathogenic nematodes decreases the effective target area for nematicidal compounds and has resulted in the development of nematicidal compounds with exquisitely high neurotoxic properties. Furthermore, because phytopathogenic nematodes are found in soil or plant roots, exposing the phytopathogenic nematodes to control agents is difficult to achieve and puts the water table at risk of contamination from those toxic compounds. The use of nematicides based on neurotoxins has been demonstrated to contaminate both ground and surface water. Consequently, many of these compounds are being removed from the market for public health reasons.

The reniform nematode, also known as *Rotylenchulus reniformis*, is the most economically important species in the genus *Rotylenchulus*. The females of reniform nematode cause extensive damage in the root system of plants by living partially inside roots. The term "reniform" refers to the kidney-shaped body of the mature females. Reniform can also cause the plants to be more susceptible to other disease-causing organisms.

Reniform nematodes parasitize the roots of a wide variety of plant species, including cotton, cowpea, sweet potato, soybean, pineapple, tea, and various vegetables such as tomato, okra, squash, and lettuce. Pathogenicity of reniform nematodes has greatly impacted agriculture. For example, they have caused a 40-60% reduction in cotton yield in Louisiana, along with an increase in *Fusarium* wilt.

Fumigation of soil prior to planting is a popular method for controlling nematodes. One of the most popular fumigants, methyl bromide, is slated for removal from use because of its ozone destroying properties. Furthermore, this practice of soil fumigation kills organisms in soil indiscriminately and runs the risk of eliminating beneficial microbes as well as disease organisms. The overall market for an effective nematicide with benign environmental effects is estimated to approach one billion dollars on a world-wide basis.

*Pasteuria* was first described in 1888 by Metchnikoff (Annales de l'Institut Pasteur 2:165-170) as a parasite of water fleas. Subsequently, Cobb described a *Pasteuria* infection of the nematode *Dorylaimus bulbiferous* (2$^{nd}$ ed. Hawaiian Sugar Planters Assoc., Expt. Sta. Div. Path. Physiol. Bull. 5:163-195, 1906).

The life cycle of the bacteria begins when endospores bind to the cuticle of the nematodes in soil. *Pasteuria* proliferate within the nematode body and pass through several documented morphological phases, including mycelial structures and thalli, culminating in the development of endospores. Endospores are released when the nematode body lyses. Growth of the bacteria within the nematode body reduces or eliminates the production of eggs by the nematode, severely restricting the rate of nematode reproduction. Economic damage to the host crop normally is inflicted by the first generation progeny of nematodes and is prevented by *Pasteuria* through lowering the concentration of progeny nematodes in the plant root zone.

While *Pasteuria* strains have been produced on multiple nematode species, such as *Meloidogyne incognita* (Verdeho, S. and R. Mankau. 1986. *Journal of Nematology,* 18:635) and *Meloidogyne arenaria* (U.S. Pat. No. 6,919,197), no *Pasteuria* strain has been observed or successfully cultivated on Reniform nematodes prior to now.

BRIEF SUMMARY

The subject invention provides a new and advantageous strain of *Pasteuria* bacteria that parasitizes Reniform nematodes. This strain has been deposited with the American Type Culture Collection and has been assigned the deposit number ATCC PTA-9643.

These bacteria are able to produce endospores that have the unique and useful property of being able to attach to, infect, grow in, re-sporulate in, and kill Reniform nematodes and other phytopathogenic nematodes.

The subject invention also includes mutants of the disclosed *Pasteuria* strain that have substantially the same or improved nematicidal properties. Procedures for making mutants are well known in the microbiological art. For example, ultraviolet light and nitrosoguanidine are used extensively toward this end.

The subject invention further pertains to variants of the exemplified microbes. The variants can be identified by, for example, polynucleotide sequences that are highly homologous with sequences from the exemplified isolate as well as by having by having the desired biological activity against Reniform nematodes.

The subject invention further includes compositions comprising a nematicidally effective amount of endospores of the disclosed *Pasteuria* bacteria strain and the use of these compositions to control phytopathogenic nematodes.

In one embodiment, a plant seed is first treated with an adherent that can adhere to the *Pasteuria* spores and/or a composition containing the spores. The adherent can be, for example, a glue and/or one or more polymers or copolymers. Examples of adherents include, but are not limited to, glues (such as ELMERS™ glue); polyvinyl acetates; silicone materials; and natural inorganic materials such as silica gel and clay.

Another aspect of the subject invention provides a seed having at least part of its surface coated with a *Pasteuria* composition, wherein the *Pasteuria* composition comprises an effective amount of *Pasteuria* spores for nematode control.

BRIEF DESCRIPTION OF THE SEQUENCES

SEQ ID NO:1 is a partial 16S rDNA sequence of the bacterium according to one embodiment of the invention.

SEQ ID NO:2 is a partial sequence of spoIIAB of the bacterium according to one embodiment of the invention.

SEQ ID NO:3 is a partial sequence of atpA of the bacterium according to one embodiment of the invention.

SEQ ID NO:4 is a partial sequence of atpF of the bacterium according to one embodiment of the invention.

DETAILED DISCLOSURE

The novel bacterial strain of the subject invention has nematicidal activity against phytopathogenic nematodes including Reniform nematodes. A culture of the microbe has been deposited with the American Type Culture Collection (ATCC), 10801 University Blvd., Manassas, Va. 20110-2209 USA. The deposit has been assigned accession number ATCC No. PTA-9643 by the repository and was deposited on Dec. 4, 2008.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

As used herein, reference to "isolated" means that the strain is removed from the environment in which it exists in nature. Thus, the isolated strain may exist as, for example, a biologically pure culture, or as spores (or other forms of the strain) in association with an agricultural carrier.

As used herein, the term "comprising" further contemplates scenarios in which the composition and/or method "consists of" or "consists essentially of" the recited components and/or steps. As used herein, reference to "consists essentially of" refers to the situation where additional components and/or steps are only those that do not affect the pesticidal activity of the composition and/or method.

"A nematicidally effective amount" as used herein refers to an amount of *Pasteuria* spores capable of killing, controlling, or infecting nematodes; retarding the growth or reproduction of nematodes; reducing a nematode population; and/or reducing damage to plants caused by nematodes.

In specific embodiments, the subject invention provides bacterial strain. ATCC PTA-9643 and mutants thereof. Procedures for making mutants are well known in the microbiological art. For example, ultraviolet light and nitrosoguanidine are used extensively toward this end. This strain has been verified to be a novel *Pasteuria* strain. SEQ ID NOs:1-4 are polynucleotide sequences of certain genes of the bacteria of the subject invention.

In other aspects, the invention provides variants of ATCC PTA-9643 having nematicidal activity. In one embodiment a "variant" has a polynucleotide sequence that hybridizes under high stringency with at least one, preferably, 2, 3, or all 4 of SEQ ID NO:1-4.

"Hybridization" refers to a reaction in which one or more polynucleotides react to form a complex that is stabilized via hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. Various degrees of stringency of hybridization can be employed. The more severe the conditions, the greater the complementarity that is required for duplex formation. Severity of conditions can be controlled by temperature, probe concentration, probe length, ionic strength, time, and the like.

Preferably, hybridization is conducted under high stringency conditions by techniques well known in the art, as described, for example, in Keller, G. H. & M. M. Manak, *DNA Probes*, and the companion volume *DNA Probes: Background. Applications, Procedures* (various editions, including $2^{nd}$ Edition, Nature Publishing Group, 1993). Hybridization is also described extensively in the Molecular Cloning manuals published by Cold Spring Harbor Laboratory Press, including Sambrook & Russell, *Molecular Cloning: A Laboratory Manual* (2001). Each of these publications is incorporated herein by reference in its entirety.

A non-limiting example of high stringency conditions for hybridization is at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C. A non-limiting example of hybridization conditions are conditions selected to be about 1, 2, 3, 4, 5, 6, 7, 8, 9, 10, 11, 12, 13, 14, 15, 16, 17, 18, 19, 20, 21, 22, 23, 24, or 25° C. lower than the thermal melting point ($T_m$) for the specific sequence in the particular solution. $T_m$ is the temperature (dependent upon ionic strength and pH) at which 50% of the target sequence hybridizes to a perfectly matched probe. $T_m$ typically increases with [Na$^+$] concentration because the sodium cations electrostatically shield the anionic phosphate groups of the nucleotides and minimize their repulsion. The washes employed may be for about 5, 10, 15, 20, 25, 30, or more minutes each, and may be of increasing stringency if desired.

Calculations for estimating $T_m$ are well-known in the art. For example, the melting temperature may be described by the following formula (Beltz, G. A., K. A. Jacobs, T. H. Eickbush, P. T. Cherbas, and F. C. Kafatos, Methods of Enzymology, R. Wu, L. Grossman and K. Moldave [eds.] Academic Press, New York 100:266-285, 1983).

$$Tm=81.5° C.+16.6 \text{ Log }[Na+]+0.41(\% G+C)-0.61(\% \text{ formamide})-600/\text{length of duplex in base pairs.}$$

A more accurate estimation of $T_m$ may be obtained using nearest-neighbor models. Breslauer, et al., *Proc. Natl. Acad. Sci. USA*, 83:3746-3750 (1986); SantaLucia, *Proc. Natl Acad. Sci. USA*, 95: 1460-1465 (1998); Allawi & SantaLucia, *Biochemistry* 36:10581-94 (1997); Sugimoto et al., *Nucleic Acids Res.*, 24:4501-4505 (1996). $T_m$ may also be routinely measured by differential scanning calorimetry (Duguid et al., *Biophys J*, 71:3350-60, 1996) in a chosen solution, or by other methods known in the art, such as UV-monitored melting. As the stringency of the hybridization conditions is increased, higher degrees of homology are obtained.

Typical methods that can be used to identify the presence of the DNA sequence as described herein include and are not limited to detecting a specific DNA sequence hybridization using specific oligonucleotides, direct DNA sequencing, restriction enzyme digest, RNase protection, chemical cleavage, and ligase-mediated detection.

An example of a variant of ATCC PTA-9643 is a strain containing a polynucleotide that has greater than 85, 90, 95, 98, or 99% sequence identity to any or all of SEQ ID NOS: 1-4.

The crystal structure of an F1-Atpase is given by Stocker et al., *Structure* 15(8):904-914 (2007) and the function of F1-Atpase has been extensively studied. See, e.g., Itoh et al., "Mechanically driven ATP synthesis by F1-Atpase," *Nature* 427(6973):407-8 (2004), as well as the references cited therein. In certain embodiments of the invention, the variant sequences of atpA encode a polypeptide that retains at least 1, 2, 3, 4, 5, or all of the differences of SEQ ID NO:4 relative to the corresponding portion of NCBI gi 93007315 from *Pasteuria ramosa*.

The spoIIAB protein is an anti-sigma factor. Duncan & Losick, *Proc Natl Acad Sci USA*, 90(6): 2325-2329 (1993). A variety of crystal structures are available. Masuda et al., *J Mol Biol*, 340(5):941-956 (2004); Campbell et al., *Cell*, 108(6): 795-807 (2002). In certain embodiments of the invention, the variant sequences of spoIIAB encode a polypeptide that retains at least 1, 2, 3, 4, 5, or all differences of SEQ ID NO:2 relative to the corresponding portion of NCBI gi 30173229 from *Pasteuria penetrans* and/or NCBI gi 93007308 from *Pasteuria ramosa*.

Structural and functional data for *E. coli* ATP synthase b subunit is given, for example, by Del Rizzo et al., *J Mol Biol*, 364(4):735-46 (2006); and Claggett et al., *J Bacteriol*, 189 (15):5463-5471 (2007). In certain embodiments of the invention, the variant sequences of atpF encode a polypeptide that retains at least 1, 2, 3, 4, 5, or all differences of SEQ ID NO:3 relative to the corresponding portions of NCBI gi 41019057 from *Pasteuria penetrans* and/or NCBI gi 93007313 from *Pasteuria ramosa*.

In certain embodiments of the invention, strains of *Pasteuria penetrans* that parasitize reniform nematodes are those *Pasteuria* strains that are phylogenetically more closely related to ATCC PTA-9643 than to any currently known *Pasteuria* strain (or, alternatively, more closely related to ATCC PTA-9643 than to any known non-reniform-parasitizing *Pasteuria penetrans* strain), as determined by routine analysis of 16s ribosomal sequences. A variety of tools and data suitable for analysis of 16s rDNA are known in the art. The following accession numbers returned by NCBI Blast of database "nr" provide 16s ribosomal sequences referenced by NCBI gi number: 157357381; 145690675; 55168340; 215499254; 29169172; 197777542; 153816650; 189353846; 154483090; 27360487; 153816533; 27359371; 10039641; 153816651; 153813776; 169191254; 77959837; 223489039; 224155181; 197766214; 197782632; 223475320; 165924309; 225111262; 50363539; 169189407; 119632772; 167630417; 147836457; 321193; 47570202; 229499565; 29565682; 5531888; 27360062; 197763227; 121592110; 227495267; 3256603; 197781048; 154500167; 154500794; 150251526; 197735635; 153813782; 167425567; 212632978; 15921449; 218151942; 163781875; 169869672; 78033426; 157354103; 40062645; 115762746; 83595848; 196018328; 115379816; 1780806; 198417694; 154500170; 108707408; 224033543; 223947683; 226443382; 237831283; 195614328; 194703406; 212274346; 149633895; 118086080; 119178984; 74007189; 197768010; 191162148; 219461701; 169213810; 167630416; 19927; 196018322; 182701819; 156341374; 115467400; 126433538; 119190145; 56422945; 50545958; 223466311; 212507121; 197762411; 169194840; 192291641; 152012802; 3831447; 67903352; 3256604; 171686416; 158294661; 154273901; 119720343. In certain embodiments of the invention, the variant sequences of 16s rDNA encode RNA that retains at least 1, 2, 3, 4, 5, or all differences relative to one or more (or any combination) of the 16s rDNA sequences set forth in this paragraph. In certain embodiments, the 16s rDNA sequences set forth by NCBI gi number in this paragraph may be excluded from the claimed invention.

Large quantities of these bacteria can be produced using fermentation techniques. Sporulation occurs from the late vegetative phase of the bacteria with production of mature, dormant spores. *Pasteuria* endospores are not damaged by drying. Therefore, they can be stored for long periods at room temperature.

Methods for growing *Pasteuria* are known in the art and include, for example, the methods described in U.S. Pat. Nos. 5,094,954 and 7,067,299, both of which are incorporated herein by reference in their entirety.

The subject invention further provides bacterial endospore compositions useful for pest control. Specifically exemplified are endospore compositions of bacteria that are pathogenic to nematodes and grow in, or on, live nematode tissue.

The endospores can be formulated into a wettable powder, liquid concentrate, granules or other formulations by the addition of surfactants, dispersants, inert carriers and other components to obtain a nematicidal composition that facilitates handling and application for particular target nematodes.

The commercial preparation would have a high concentration of endospores, typically in excess of $1 \times 10^7$ spores/ml and preferably in excess of $1 \times 10^9$ spores per ml or gram of dry product.

The composition can also include one or more of the following ingredients: other pesticides, including compounds which act only below the ground; fungicides, such as captan, thiram, metalaxyl, fludioxonil, oxadixyl, and isomers of each of those materials, and the like; herbicides, including compounds selected from carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi.

These formulation and application procedures are all well known in the art and are used with commercial strains of *Pasteuria*. The nematicidal composition can be sprayed or applied onto foliage to control phytopathogenic nematodes.

Another approach that can be taken is to incorporate the endospores into granules, optionally containing an attractant, and applying these granules to the soil for control of the soil-dwelling nematodes. Typically, upon contact with water the spores are released from the granule and then the spores adhere to, and infect, nematodes. Formulated spores can also be applied as a seed-coating for root treatment or total plant treatment.

The amount of the endospores applied needs to be nematicidally effective. In one embodiment, less than one quart of the endospores per acre is sufficient to achieve effective nematode control.

Advantageously, the compositions are easy to apply with conventional application equipment. The endospore's mode of action makes the development of resistance unlikely. Most available nematicides must be applied to the soil before planting, because the chemicals would otherwise harm the plants. By contrast, this *Pasteuria* strain will not damage the plants, and can be applied at any time.

Another aspect of the invention provides seeds treated with the subject *Pasteuria* composition. One embodiment provides seeds having at least part of the surface area coated with the *Pasteuria* composition. In a specific embodiment, the *Pasteuria* treated seeds have a spore concentration from about $10^6$ to about $10^9$ spores per seed. The seeds may also have more spores per seed, such as, for example $1 \times 10^{10}$, $1 \times 10^{11}$ or $1 \times 10^{12}$ spores per seed.

The materials and methods of the subject invention can be used for reducing damage to plant species, including, but not limited to, green beans, turf grasses, sweet potato, tomatoes, cotton, corn, soy beans, okra, lettuce, squash, vegetables, pine apple, tea, wheat, barley, rice and canola.

Following is an example, which illustrates procedures for practicing the invention. This example should not be construed as limiting. All percentages are by weight and all solvent mixture proportions are by volume unless otherwise noted.

EXAMPLE 1

Seed Treatments

In accordance with the subject invention, *Pasteuria* spores can be effectively delivered to control phytopathogenic nematodes by coating the *Pasteuria* spores on plant seeds.

The *Pasteuria* spores can be coated freely onto the seeds or, preferably, they can be formulated in a liquid or solid composition before being coated onto the seeds. For example, a solid composition comprising the spores can be prepared by mixing a solid carrier with a suspension of the spores until the solid carriers are impregnated with the spore suspension. This mixture can then be dried to obtain the desired particles.

The solid carriers are preferably granules. The granules can be, for example, diatomaceous earth granules from AXIS® and/or greensgrade clay granules from PROFIL®. Various additives, such as adherents, dispersants, surfactants, and nutrient and buffer ingredients, can also be included in the carrier and spore suspension mixture.

In a specific embodiment, in addition to the spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum arabics; gelatins; syrups; and starches. More examples can be found in, for example, U.S. Pat. No. 7,213,367, which is incorporated by reference herein in its entirety.

The adherent layer can help attach the spores on the surface of the seed and prevent possible drop-offs. In addition, the coating can also comprise other chemical or biological agents having a beneficial effect in combination with the *Pasteuria* spores for nematode control and/or for control of other pests. The coatings may also include fertilizers and other components that help promote seed germination, and/or plant growth and/or health.

Thus, the subject invention provides a method of making a *Pasteuria* spore coating on a plant seed. In a specific embodiment, the method comprises combining dried granule mixtures impregnated with *Pasteuria* spores and a seed coated with an adherent.

Although the seed treatments can be applied to a seed in any physiological state, it is preferred that the seed be in a sufficiently durable state that it incurs no damage during the treatment process. Typically, the seed has been harvested from the field; removed from the plant; and separated from any other non-seed plant material. The seed is preferably biologically stable to the extent that the treatment does not cause biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the *Pasteuria* spore composition. Within the limitations just described, the treatment can be applied to the seed at any time between harvest of the seed and sowing of the seed. As used herein, the term "unsown seed" is meant to include seed at any period between the harvest of the seed and the sowing of the seed in the ground for the purpose of germination and growth of the plant.

As used herein, when it is said that unsown seed is "treated" with the *Pasteuria*-containing composition, such treatment is not meant to include those practices in which *Pasteuria* are applied to the soil, rather than to the seed.

The *Pasteuria* spores are typically applied to the seeds in the form of a pesticide formulation. This formulation may contain one or more other desirable components including but not limited to liquid diluents, binders, fillers for protecting the seeds during stress conditions, and plasticizers to improve flexibility, adhesion and/or spreadability of the coating. In addition, it may be desirable to add to the formulation drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan, having the benefit of the current disclosure, can readily select desirable components to use in the formulation.

The seeds may also be treated with one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed or alternatively may be added as part of the *Pasteuria* composition.

Preferably, the amount of the novel composition or other ingredients used in the seed treatment should not inhibit germination of the seed, or cause phytotoxic damage to the seed.

The formulation that is used to treat the seed in the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is preferably about 0.5% to about 99% by weight (w/w), preferably 5-40% or as otherwise formulated by those skilled in the art.

As mentioned above, other conventional inactive or inert ingredients can be incorporated into the formulation. Such inert ingredients include but are not limited to: conventional sticking agents; dispersing agents such as methylcellulose (Methocel A15LV or Methocel A15C, for example, serve as combined dispersant/sticking agents for use in seed treatments); polyvinyl alcohol (e.g., Elvanol 51-05); lecithin (e.g., Yelkinol P), polymeric dispersants (e.g., polyvinylpyrrolidone/vinyl acetate PVPIVA S-630); thickeners (e.g., clay thickeners such as Van Gel B to improve viscosity and reduce settling of particle suspensions); emulsion stabilizers; surfactants; antifreeze compounds (e.g., urea), dyes, colorants, and the like. Further inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

The coating formulations of the present invention can be applied to seeds by a variety of methods, including, but not limited to, mixing in a container (e.g., a bottle or bag), mechanical application, tumbling, spraying, and immersion. A variety of active or inert material can be used for contacting seeds with pesticides according to the present invention, such as conventional film-coating materials including but not limited to water-based film coating materials such as SEPIRET™ (Seppic, Inc., Fairfield, N.J.) and OPACOAT™ (Berwind Pharm. Services, Westpoint, Pa.).

Seed coating methods and compositions that are known in the art are useful when they are modified by the addition of one of the embodiments of the present invention. Such coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

The amount of *Pasteuria* that is used for the treatment of the seed will vary depending upon the type of seed and the type of active ingredients, but the treatment will comprise contacting the seeds with an amount of the *Pasteuria* that is pesticidally effective. As used herein, a nematicidally effective amount means that amount of *Pasteuria* that will kill the nematodes, or will consistently reduce or retard the amount of damage caused by nematodes.

The pesticides that are used in the treatment must not inhibit germination of the seed and should be efficacious in protecting the seed and/or the plant during that time in the nematode's life cycle in which it causes injury to the seed or plant. In general, the coating will be efficacious for approximately 1 hour to 120 days after sowing.

The coatings formed with the pesticide are preferably of the type that are capable of effecting a slow rate of release of the pesticide by diffusion or movement through the matrix to the surrounding medium.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the pesticidal coating layer.

The pesticide formulation may be applied to the seeds using a variety of techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The *Pasteuria* treated seeds may also be enveloped with a film overcoating to protect the coating. Such overcoatings are known in the art and may be applied using fluidized bed and drum film coating techniques.

In another embodiment of the present invention, the *Pasteuria* spores can be introduced onto a seed by use of solid matrix priming. For example, a quantity of the *Pasteuria* spores can be mixed with a solid matrix material and then the seed can be placed into contact with the solid matrix material for a period to allow the pesticide to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the pesticide for a time and releasing that pesticide into or onto the seed. It is useful to make sure that the pesticide and the solid matrix material are compatible with each other. For example, the solid matrix material should be chosen so that it can release the pesticide at a reasonable rate, for example over a period of minutes, hours, or days.

Unlike the vegetative form of the bacteria, *Pasteuria* spores are not damaged by drying and they can be stored for long periods at room temperature. Therefore, one advantage of the subject invention is that the drying and other harsh steps used in coating methods can be applied to the subject invention for seed coating without significantly reducing the effectiveness of the spores. The long shelf life of seeds of the subject invention also allows variations in planting schedules. In addition, the survival rate of the *Pasteuria* spores is much higher than the vegetative form of the bacteria during transport and sowing once placed in the soil.

In general, the effective amount of spores range from about $1 \times 10^5$ to $1 \times 10^{12}$ (or more) spores/seed. Preferably, the spore concentration is about $1 \times 10^6$ to about $1 \times 10^9$ spores/seed.

In one embodiment, to obtain the granule mixtures, the ratio of *Pasteuria* spores to granule is about $3 \times 10^7$ to $5 \times 10^7$ spores/g granules. In a specific embodiment, about 3-5 ml of a *Pasteuria* spore suspension containing about $2 \times 10^7$ spores/ml of buffer is added to about 2 g of granules. The ratio can depend on the granule types. For example, about 5 ml of spore suspension can be applied to 2 g of AXIS® granules while about 3 ml of spore suspension is preferred for the same amount of PROFILE® granules. The adherent can be any commercial glue biocompatible with the seed and soil, such as Elmer's clear school glue containing polyvinyl acetate.

An extra heat-treatment step can be included in order to kill nematodes if the spores are produced in nematode hosts. The heat-treatment step can be applied to the spore suspension before mixing with granules. Alternatively, the step can be applied after formation of granule mixtures.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An biologically pure *Pasteuria* strain that is deposited as ATCC accession number PTA-9643, or which is a nematicidally active mutant of said deposited strain ATCC accession number PTA-9643, wherein said nematicidally active mutant has all of the identifying characteristics of said deposited strain ATCC accession number PTA-9643, and wherein said nematicidally active mutant comprises the polynucleotide sequence that is at least 95% identical to SEQ ID NO:2 or SEQ ID NO:3.

2. The biologically pure *Pasteuria* strain, according to claim 1, wherein said mutant has the polynucleotide sequence that is at least 95% identical to SEQ ID NO:2.

3. The biologically pure *Pasteuria* strain, according to claim 1, which is active against a reniform nematode.

4. The biologically pure *Pasteuria* strain, according to claim 1, wherein said variant mutant has the polynucleotide sequence that is at least 95% identical to SEQ ID NO:3.

5. A biologically pure *Pasteuria* strain that is deposited as ATCC accession number PTA-9643, or which is a nematicidally active mutant of said deposited strain ATCC accession number PTA-9643, wherein said nematicidally active mutant has all of the identifying characteristics of said deposited strain ATCC accession number PTA-9643, and wherein said mutant has the polynucleotide sequences that are at least 99% identical to each of SEQ ID NOS:1-4.

* * * * *